United States Patent
Ostreicher

(10) Patent No.: US 8,851,887 B1
(45) Date of Patent: Oct. 7, 2014

(54) INTRA-ORAL MOUTH VIBRATOR

(71) Applicant: David Ostreicher, Levittown, NY (US)

(72) Inventor: David Ostreicher, Levittown, NY (US)

( * ) Notice: Subject to any disclaimer, the term of this patent is extended or adjusted under 35 U.S.C. 154(b) by 0 days.

(21) Appl. No.: 13/935,500

(22) Filed: Jul. 4, 2013

(51) Int. Cl.
*A61C 7/08* (2006.01)
*A61C 19/06* (2006.01)
*A61H 1/00* (2006.01)

(52) U.S. Cl.
CPC . *A61C 19/06* (2013.01); *A61H 1/00* (2013.01)
USPC ............... 433/6; 433/215; 433/229; 601/46

(58) Field of Classification Search
USPC .......... 433/2–3, 5, 6, 8–9, 18, 24, 37, 41–48, 433/215, 229, 86, 118–119, 36, 32, 216; 601/139–142, 38, 46–83; 128/861–862; 606/234–235
See application file for complete search history.

(56) References Cited

U.S. PATENT DOCUMENTS

| | | | |
|---|---|---|---|
| 1,826,434 A | 10/1931 | Reiss | |
| 4,123,844 A | 11/1978 | Kurz | |
| 5,030,098 A * | 7/1991 | Branford | 433/215 |
| 6,633,747 B1 * | 10/2003 | Reiss | 455/41.2 |
| 2009/0061375 A1 * | 3/2009 | Yamamoto et al. | 433/6 |
| 2010/0055634 A1 * | 3/2010 | Spaulding et al. | 433/5 |
| 2011/0076634 A1 * | 3/2011 | Yamamoto et al. | 433/18 |
| 2013/0004912 A1 * | 1/2013 | Brown et al. | 433/86 |

* cited by examiner

*Primary Examiner* — Edward Moran
(74) *Attorney, Agent, or Firm* — Donald J. Ersler

(57) ABSTRACT

An intra-oral mouth vibrator preferably includes a lower bite pad, an upper bite pad, a retention pad, at least two vibratory motors and a power source. Two holes are formed through the upper bite pad to receive the two vibratory motors. One end of a wire is connected to the two vibratory motors to supply power thereto. The other end of the wire is connected to a power source. The retention pad preferably includes a perimeter retention lip. The upper bite pad is placed on a top of the lower bite pad. The upper and lower bite pads are inserted into the retention pad. In use, the vibratory motors receive electrical power from the power source, which causes the at least two vibratory motors to vibrate. The vibration causes the lower bite pad, the upper bite pad and the retention pad to vibrate.

15 Claims, 3 Drawing Sheets

INTRA-ORAL MOUTH VIBRATOR

BACKGROUND OF THE INVENTION

1. Field of the Invention

The present invention relates generally to orthodontics and more specifically to an intra-oral mouth vibrator, which aids movement and reduces discomfort of teeth.

2. Discussion of the Prior Art

U.S. Pat. No. 1,826,434 to Reiss discloses a vibrating device. U.S. Pat. No. 4,123,844 to Kurz discloses a vibrational mouth pad orthodontic appliance. U.S. Pat. No. 5,030,098 to Branford discloses a vibratory dental mouthpiece.

Accordingly, there is a clearly felt need in the art for an intra-oral mouth vibrator, which aids movement and reduces discomfort of teeth.

SUMMARY OF THE INVENTION

The present invention provides an intra-oral mouth vibrator, which aids movement and reduces discomfort of teeth. The intra-oral mouth vibrator preferably includes a lower bite pad, an upper bite pad, a retention pad, at least two vibratory motors and a power source. The lower bite pad, the upper bite pad and the retention pad preferably have a substantial C-shape, but could also have a D-shaped perimeter. Two holes are preferably formed through the upper bite pad to receive the two vibratory motors. The holes are preferably located at substantially a front of the upper bite pad. One end of a two-conductor wire is connected to the two vibratory motors to supply power thereto. The other end of the two conductor wire is connected to a power source. The retention pad includes a perimeter retention lip. The upper bite pad is placed on a top of the lower bite pad. The upper and lower bite pads are inserted into perimeter retention lip of the retention pad. In use, intra-oral mouth vibrator is inserted into a human mouth and clamped between the upper and lower teeth. The vibratory motors receive electrical power from the power source, which causes the at least two vibratory motors to vibrate. The vibration causes the lower bite pad, the upper bite pad and the retention pad to vibrate, which aids movement and reduces discomfort of teeth.

Accordingly, it is an object of the present invention to provide an intra-oral mouth vibrator, which aids movement and reduces discomfort of teeth.

These and additional objects, advantages, features and benefits of the present invention will become apparent from the following specification.

DETAILED DESCRIPTION OF THE PREFERRED EMBODIMENTS

Figure 1:
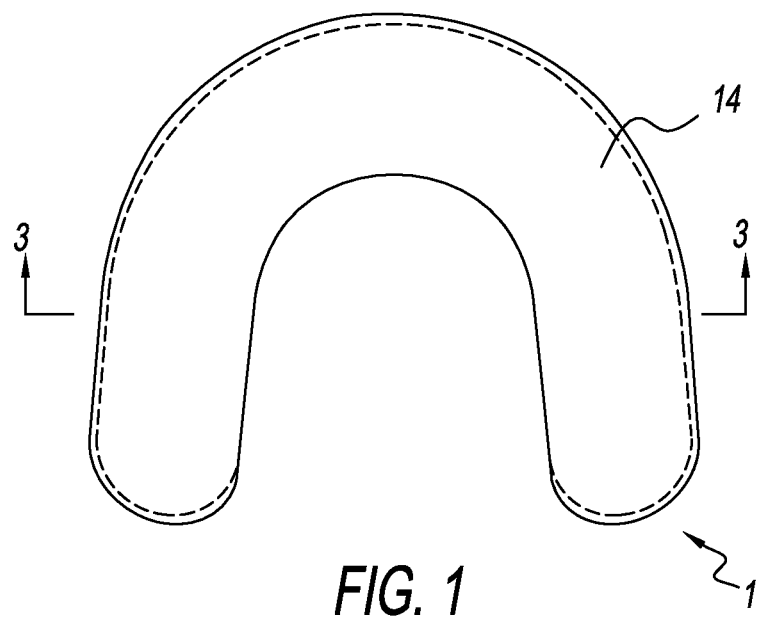
FIG. 1 is a top view of an intra-oral mouth vibrator in accordance with the present invention.
Figure 2:
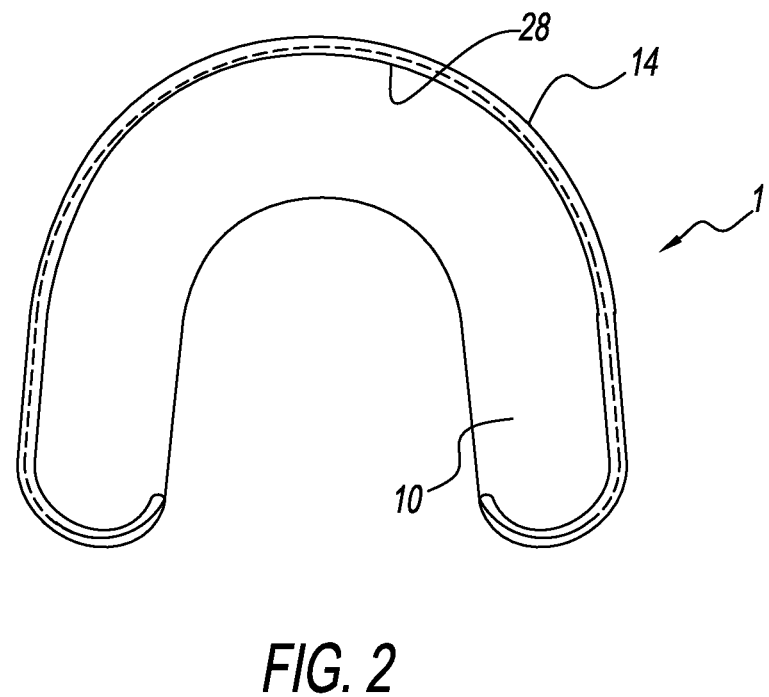
FIG. 2 is a bottom view of an intra-oral mouth vibrator in accordance with the present invention.
Figure 3:
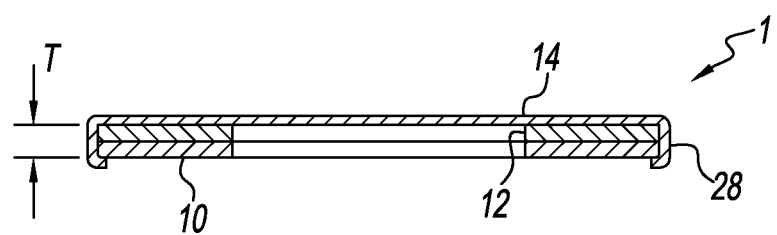
FIG. 3 is a cross-sectional end view of an intra-oral mouth vibrator in accordance with the present invention.
Figure 4:
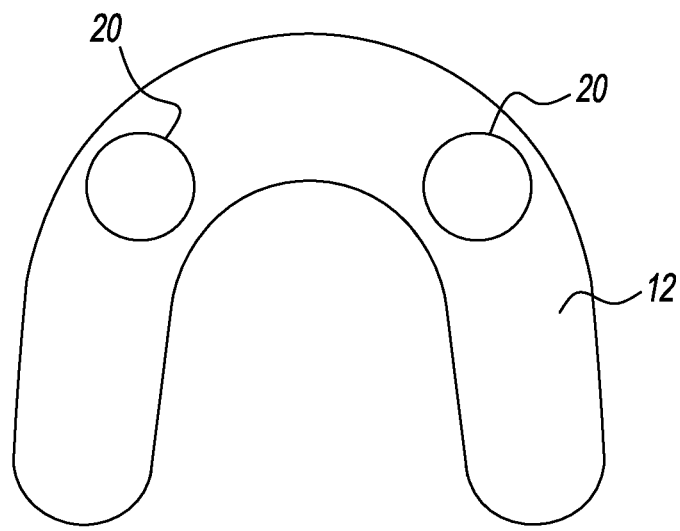
FIG. 4 is a top view of an upper bite pad, before insertion of two vibratory motors of an intra-oral mouth vibrator in accordance with the present invention.
Figure 5:
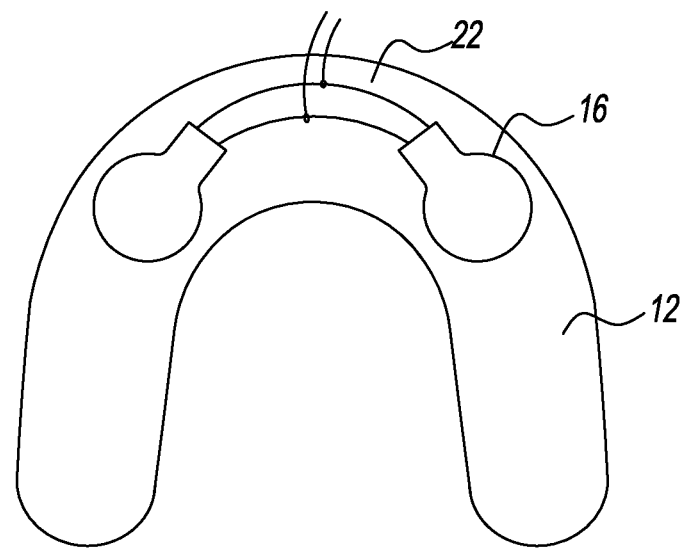
FIG. 5 is a bottom view of an upper bite pad, after insertion of two vibratory motors of an intra-oral mouth vibrator in accordance with the present invention.

With reference now to the drawings, and particularly to FIG. 1, there is shown a top view of an intra-oral mouth vibrator 1. With reference to FIGS. 2-5, the intra-oral mouth vibrator 1 preferably includes a lower bite pad 10, an upper bite pad 12, a retention pad (upper contact pad) 14, at least two vibratory motors 16 and a power source 18. The lower bite pad 10, the upper bite pad 12 and the retention pad 14 preferably have a substantial C-shape, but could have a D-shaped perimeter. The lower and upper bite pads are preferably elasti-bite therapy wafers, which may be purchased from the website of Ortho-Direct. The elasti-bite therapy wafers are commonly used to treat teeth by allowing the pad to be compressed, when biting thereof. The lower and upper bite pads are elastic. However, other therapy wafers may also be used. The retention pad 14 is preferably fabricated from Essix C+ plastic, which may be purchased from essix.com. The Essix C+ plastic is commonly used to create teeth retainers. However, other types of plastic may also be used.

Figure 6:
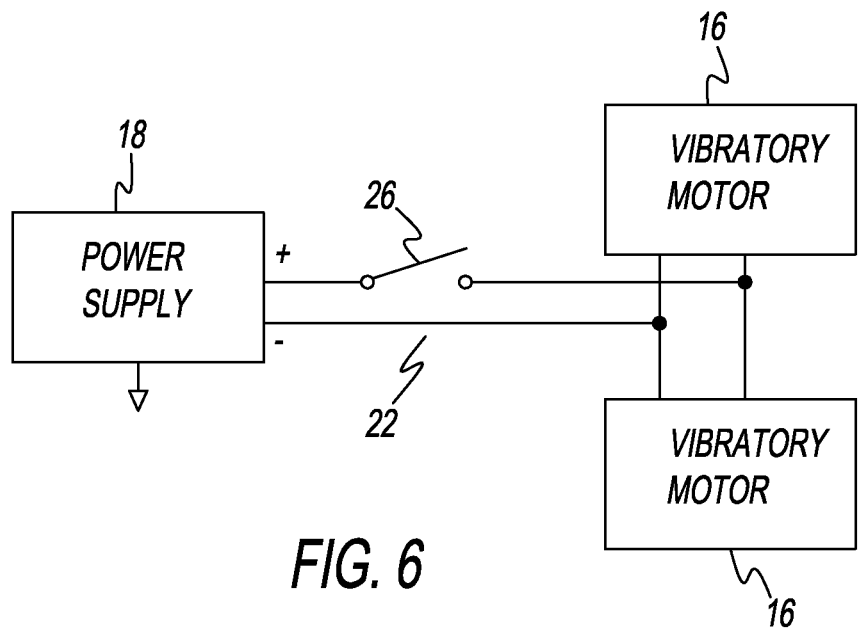
FIG. 6 is an electrical schematic of an intra-oral mouth vibrator in accordance with the present invention.

Two motor holes 20 are formed through the upper bite pad 12 to receive the two vibratory motors 16. The two motor holes 20 are preferably located at substantially a front of the upper bite pad. The motor holes 20 are sized to receive an outside perimeter of the vibratory motor 18. The vibratory motor 18 is preferably a VPM2 vibrating disk motor, which may be purchased from roboshop.com. The two vibratory motors 18 are inserted into the two motor holes 20. With reference to FIG. 6, one end of a two-conductor wire 22 is connected to the two vibratory motors 18 to supply power thereto. The other end of the two-conductor wire 22 is connected to a power source 24 through a power switch 26.

The retention pad 14 includes a perimeter retention lip 28. An inner thickness "T" of the perimeter retention lip 28 is sized to receive a thickness of the lower and upper bite pads. The upper bite pad 12 is placed on a top of the lower bite pad 10. The upper and lower bite pads are inserted into the perimeter retention lip 28 of the retention pad 14. However, the lower bite pad 10, the upper bite pad 12 and the retention pad 14 could be attached to each other with adhesive or any other suitable attachment device or method.

In use, intra-oral mouth vibrator 1 is inserted into a human mouth. The power source 18 supplies power to the two vibratory motors 16 through the two-conductor wire 22, when the power switch 26 is closed. The power source 18 is preferably a DC power source in the form of two AA batteries, but other power sources could also be used. Electrical power from the power source 18 causes the two vibratory motors 16 to vibrate. The vibration causes the lower bite pad 10, the upper bite pad 12 and the retention pad 14 to vibrate, which aids movement and reduces discomfort of teeth.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. An intra-oral mouth vibrator comprising:
    a lower bite pad being fabricated from an elastic material;
    an upper bite pad being in contact with said lower bite pad;
    a retention pad having an outer perimeter lip, said outer perimeter lip sized to receive and retain said lower bite pad and said upper bite pad, said outer perimeter lip further comprising a retention portion extending below said lower bite pad, said retention portion retaining said lower bite pad and said upper bite pad against a bottom surface of said retention pad, wherein said lower bite pad and upper bite pad may be inserted into said retention pad; and at least two vibratory motors located in at least two holes in said upper bite pad, wherein power is supplied to said at least two vibratory motors to vibrate said lower bite pad and said retention pad.

2. The intra-oral mouth vibrator of claim 1 wherein:
said at least two holes are located near a front of said upper bite pad.

3. The intra-oral mouth vibrator of claim 1, further comprising:
a power supply for supplying electrical power to said at least two vibratory motors.

4. The intra-oral mouth vibrator of claim 3, further comprising:
a power switch for controlling the flow of electrical power to said at least two vibratory motors from said power supply.

5. An intra-oral mouth vibrator comprising:
a lower bite pad being fabricated from an elastic material, said lower bite pad having a substantial C-shape;
an upper bite pad being in contact with said lower bite pad, said upper bite pad having a substantial C-shape;
a retention pad having an outer perimeter lip, said outer perimeter lip sized to receive and retain said lower bite pad and said upper bite pad, said outer perimeter lip further comprising a retention portion extending below said lower bite pad, said retention portion retaining said lower bite pad and said upper bite pad against a bottom surface of said retention pad, wherein said lower bite pad and upper bite pad may be inserted into said retention pad and; and
at least two vibratory motors located in at least two holes in said upper bite pad, wherein power is supplied to said at least two vibratory motors to vibrate said lower bite pad and said retention pad.

6. The intra-oral mouth vibrator of claim 5 wherein:
said at least two holes are located near a front of said upper bite pad.

7. The intra-oral mouth vibrator of claim 5, further comprising:
a power supply for supplying electrical power to said at least two vibratory motors.

8. The intra-oral mouth vibrator of claim 7, further comprising:
a power switch for controlling the flow of electrical power to said at least two vibratory motors from said power supply.

9. An intra-oral mouth vibrator comprising:
a lower bite pad being fabricated from an elastic material;
an upper bite pad being in contact with said lower bite pad;
a retention pad having an outer perimeter lip, said outer perimeter lip sized to receive and retain said lower bite pad and said upper bite pad, said outer perimeter lip further comprising a retention portion extending below said lower bite pad, said retention portion retaining said lower bite pad and said upper bite pad against a bottom surface of said retention pad, wherein said lower bite pad and upper bite pad may be inserted into said retention pad; and
at least two vibratory motors located in at least two holes in said upper bite pad, said at least two vibratory motors include a round outer perimeter, wherein power is supplied to said at least two vibratory motors to vibrate said lower bite pad and said retention pad.

10. The intra-oral mouth vibrator of claim 9 wherein:
said at least two holes are located near a front of said upper bite pad.

11. The intra-oral mouth vibrator of claim 9, further comprising:
a power supply for supplying electrical power to said at least two vibratory motors.

12. The intra-oral mouth vibrator of claim 11, further comprising:
a power switch for controlling the flow of electrical power to said at least two vibratory motors from said power supply.

13. The intra-oral mouth vibrator of claim 1 wherein:
said at least two vibratory motors are insertable into said upper bite pad.

14. The intra-oral mouth vibrator of claim 5 wherein:
said at least two vibratory motors are insertable into said upper bite pad.

15. The intra-oral mouth vibrator of claim 9 wherein:
said at least two vibratory motors are insertable into said upper bite pad.

* * * * *